United States Patent
Kellnberger et al.

(10) Patent No.: US 12,064,213 B2
(45) Date of Patent: Aug. 20, 2024

(54) MEDICAL APPARATUS AND SYSTEM

(71) Applicant: Siemens Healthcare GmbH, Erlangen (DE)

(72) Inventors: Stephan Kellnberger, Erlangen (DE); Alois Regensburger, Poxdorf (DE)

(73) Assignee: Siemens Healthineers AG, Forchheim (DE)

( * ) Notice: Subject to any disclaimer, the term of this patent is extended or adjusted under 35 U.S.C. 154(b) by 284 days.

(21) Appl. No.: 17/498,047

(22) Filed: Oct. 11, 2021

(65) Prior Publication Data

US 2022/0125318 A1 Apr. 28, 2022

(30) Foreign Application Priority Data

Oct. 22, 2020 (DE) ..................... 10 2020 213 348.4

(51) Int. Cl.
*A61B 5/00* (2006.01)
*A61B 1/018* (2006.01)

(52) U.S. Cl.
CPC .......... *A61B 5/0095* (2013.01); *A61B 5/6848* (2013.01); *A61B 5/7425* (2013.01); *A61B 1/018* (2013.01)

(58) Field of Classification Search
CPC .................................................. A61B 5/0095
See application file for complete search history.

(56) References Cited

U.S. PATENT DOCUMENTS

2006/0106315 A1* 5/2006 Edens ................ A61B 17/3417
600/461
2012/0271170 A1 10/2012 Emelianov et al.
(Continued)

FOREIGN PATENT DOCUMENTS

EP 3320852 A1 5/2018
KR 20140126554 A 10/2014
(Continued)

OTHER PUBLICATIONS

Freeman, Martin L., and Nalini M. Guda. "ERCP cannulation: a review of reported techniques." Gastrointestinal endoscopy 61.1 (2005): 112-125.
(Continued)

*Primary Examiner* — Joseph M Santos Rodriguez
(74) *Attorney, Agent, or Firm* — Lempia Summerfield Katz LLC

(57) ABSTRACT

A medical apparatus having a light emission unit, an ultrasound transducer, an instrument channel, and a hollow needle is disclosed. The apparatus is configured to be arranged at least partly in an examination region of an examination object. The light emission unit is configured to emit excitation light. The excitation light is configured to excite an optoacoustic emission of ultrasound. The light emission unit is arranged at least partly in the hollow needle. The hollow needle is arranged at least partly for movement in the instrument channel. The instrument channel has an opening for bringing the hollow needle and the light emission unit out on a distal section of the apparatus. The ultrasound transducer is arranged on the distal section of the apparatus. The hollow needle is configured to move out at least partly from instrument channel through the opening. The ultrasound transducer is configured to receive the ultrasound.

13 Claims, 8 Drawing Sheets

(56) References Cited

U.S. PATENT DOCUMENTS

| | | |
|---|---|---|
| 2013/0016185 A1 | 1/2013 | Stolka et al. |
| 2016/0242737 A1 | 8/2016 | Zhou et al. |
| 2018/0132729 A1 | 5/2018 | Irisawa |
| 2018/0177408 A1* | 6/2018 | Irisawa ............... A61B 8/4416 |
| 2020/0036910 A1 | 1/2020 | Alzaga et al. |
| 2020/0155250 A1 | 5/2020 | Ghodrati et al. |
| 2020/0253673 A1 | 8/2020 | Azizian et al. |
| 2020/0261170 A1 | 8/2020 | Ziso et al. |

FOREIGN PATENT DOCUMENTS

| | | |
|---|---|---|
| WO | 2011063266 A2 | 5/2011 |
| WO | 2015054243 A1 | 4/2015 |
| WO | 2019006028 A1 | 1/2019 |

OTHER PUBLICATIONS

German Office Action for German Application No. 10 2020 213 348.4 dated Aug. 5, 2021.

* cited by examiner

MEDICAL APPARATUS AND SYSTEM

The present patent document claims the benefit of German Patent Application No. 10 2020 213 348.4, filed Oct. 22, 2020, which is hereby incorporated by reference in its entirety.

TECHNICAL FIELD

The disclosure relates to a medical apparatus and a system.

BACKGROUND

Flexible endoscopes are frequently used for treatment and/or examination of pathological changes in a biliary system of an examination object, (e.g., gallstones and/or stenoses and/or inflammations), as part of an Endoscopic Retrograde Cholangio-Pancreatography (ERCP). In such cases an, (e.g., manual), handling of the endoscope and/or a precise navigation in an anatomy of the examination object by a user is frequently difficult, in particular, by medical operating personnel and/or by a doctor.

Frequently, a bile duct is punctured during the course of the ERCP, especially via a papilla, which connects the bile duct to the intestine. In such cases, it may be difficult for the user, (in particular, by the optical image provided by the flexible endoscope, especially without an x-ray contrast medium in the bile duct for imaging by a fluoroscopy), to detect an orientation of the bile duct using the papilla as its starting point. Disadvantageously, an incorrect puncturing, (e.g., a puncturing of the pancreatic duct), may be made more likely by this, whereby the risk of injury and inflammation may significantly increase for the examination object. Such complications may further be made more likely within the framework of an ERCP by anatomical variants of the examination object, for example, by an unusually long main bile duct.

An object of the present disclosure is therefore to specify a medical apparatus, which makes possible a safe and at the same time precise examination and/or puncturing of an examination object. An object of the disclosure is furthermore to specify a suitable system.

SUMMARY AND DESCRIPTION

The scope of the present disclosure is defined solely by the appended claims and is not affected to any degree by the statements within this summary. The present embodiments may obviate one or more of the drawbacks or limitations in the related art.

In a first aspect, the disclosure relates to a medical apparatus. In this case, the medical apparatus has a light emission unit, an ultrasound transducer, an instrument channel, and a hollow needle. Moreover, the apparatus is configured to be arranged at least partly in an examination region of an examination object. The light emission unit is further configured to emit excitation light. Furthermore, the excitation light is configured to excite an optoacoustic emission of ultrasound, in particular of optoacoustic waves. The light emission unit is further arranged at least partly in the hollow needle. Moreover, the hollow needle is arranged at least partly for movement in the instrument channel. Moreover, the instrument channel has an opening for bringing the hollow needle and the light emission unit out on a distal section of the apparatus. Moreover, the ultrasound transducer is arranged on the distal section of the apparatus. The hollow needle is further configured, for puncturing a tissue in the examination region, to be movable out at least partly from the instrument channel through the opening. In this case, the ultrasound transducer is configured for receiving ultrasound.

The medical apparatus may be configured as an elongated, diagnostic, and/or surgical instrument. In particular, the medical apparatus may be configured as a catheter and/or endoscope, e.g., as a duodenoscope. In this case, the instrument channel may advantageously run in a longitudinal extent direction of the medical apparatus at least in sections, in particular, over an entire length of the medical apparatus. The instrument channel may be an, (e.g., elongated), hollow space in an interior of the medical apparatus, which is delimited spatially by an, (e.g., cylindrical), outer casing of the medical apparatus. The outer casing of the medical apparatus may advantageously be impermeable to fluids, (e.g., bodily fluids of the examination object), and/or impermeable to light. Moreover, the medical apparatus may have a distal section configured to be arranged in the examination region of the examination object. The examination object may be a human and/or animal patient. The examination region may further include a spatial area of the examination object, which has an anatomical structure, in particular, a hollow organ. The medical apparatus, in particular the distal section, may advantageously be configured to be arranged at least partly in the hollow organ, (e.g., in a duodenum and/or a vessel section such as in an artery and/or vein).

The hollow needle may further be configured as a cannula, for example. The hollow needle may advantageously be configured rigidly and/or flexibly at least in sections. Moreover, the hollow needle may have a tipped section configured for puncturing the tissue in the examination region. Furthermore, the hollow needle, at least in sections, may be permeable to light and/or impermeable to light. The hollow needle may further have an opening on the tipped section.

The light emission unit may advantageously have a light source, (e.g., a light-emitting diode (LED) and/or a laser), which is configured for generating and/or emitting excitation light of a defined wavelength and/or of a defined wavelength range. In this case, the defined wavelength and/or the defined wavelength range may advantageously be configured and/or predetermined by a user, in particular, through a user entry by an input unit. In particular, the excitation light may have at least a narrowband and/or wideband wavelength range, e.g., in an infrared range and/or near infrared range. Furthermore, the excitation light may be configured multi-spectrally. Advantageously, the light emission unit may be configured to emit the excitation light omnidirectionally and/or spatially restricted. In particular, the light emission unit may be configured to illuminate the examination region at least partly with the excitation light.

The light emission unit, in particular the light source, may advantageously be arranged at least partly in the hollow needle, in particular in a fixed position and/or movably. In this case, the light emission unit may be configured to emit the excitation light through the light-permeable hollow needle and/or through the opening on the tipped section of the hollow needle.

Furthermore, the hollow needle may be arranged at least partly, in particular translationally and/or rotationally, movable in the instrument channel. In particular, the hollow needle may be movable translationally in the longitudinal direction of the medical apparatus in the instrument channel. The hollow needle may further be rotationally movable around the longitudinal direction of the medical apparatus in the instrument channel. The hollow needle may be configured to be moved by the user at a proximal section of the medical apparatus relative to the instrument channel. In this case, the medical apparatus may be configured to make possible the movement of the hollow needle by the user in particular directly and/or indirectly, e.g., by a control cable.

The instrument channel may further have an opening on the distal section of the apparatus for bringing out the hollow needle and the light emission unit. In this case, the opening on the distal section may advantageously be arranged in the longitudinal direction of the instrument channel and/or to the side, in particular on the cylindrical outer casing of the instrument channel. The hollow needle and the light emission unit arranged at least partly therein are advantageously configured to be movable out of the instrument channel, in particular translationally, via the opening on the distal section of the instrument channel.

In particular, the hollow needle may be configured to puncture tissue at a puncturing point in the examination region by the tipped section after it has been moved out of the opening of the instrument channel, in particular to break through it. Advantageously, the punctured tissue may surround a further hollow organ, e.g., a bile duct, wherein a fluid may be arranged in the further hollow organ, e.g., a bodily fluid and/or a contrast medium, in particular a fluorescence dye. The excitation light may advantageously be configured for an optoacoustic emission of ultrasound of the punctured tissue and/or of the fluid, which may be arranged in the further hollow organ for example.

The light emission unit may further be configured to be arranged inside and/or outside the punctured tissue. In this case, the hollow needle may be configured to bring the light emission unit into the punctured tissue, in particular the further hollow organ. In particular, the light emission unit may be configured to illuminate the punctured tissue with the excitation light via the opening of the hollow needle. As an alternative, or in addition, the light emission unit may be configured to illuminate the punctured tissue with the excitation light from outside the puncturing point.

The medical apparatus may further have an ultrasound transducer arranged on a distal section of the apparatus. In this case, the ultrasound transducer advantageously has at least one transducer element configured to detect the ultrasound, in particular the acoustic signal of the ultrasound, in the examination region. Advantageously, the ultrasound transducer, in particular the at least one transducer element, may be configured to provide a signal as a function of the received ultrasound. The ultrasound transducer, in particular the at least one transducer element, may be arranged in a fixed location and/or movably on the hollow needle and/or an outer side of the instrument channel. The ultrasound transducer may further be arranged at least partly in the instrument channel and/or be able to be brought out via the opening on the distal section of the instrument channel. In particular, the ultrasound transducer may be arranged aligned forwards and/or aligned sideways in relation to the longitudinal direction of the instrument channel.

The proposed apparatus makes possible an especially uncomplicated and at the same time direct imaging of the punctured tissue, in particular of the further hollow organ. A risk of injury to the examination object, by incorrect puncturing for example, may advantageously be reduced by the medical apparatus, in particular by the ultrasound-based imaging made possible by it.

In a further advantageous form of embodiment of the proposed apparatus, the light emission unit may have a light source and an optical fiber. In this case, the optical fiber may optically contact the light source. The optical fiber may further have an, in particular light-emitting, end area for emission of the excitation light from the light source. Furthermore, the hollow needle may be configured to bring out the end area of the optical fiber.

The optical fiber may be configured as an optical waveguide. The optical fiber may further include at least one glass fiber and/or a polymer optical fiber, in particular a fiber bundle. The light source may further be configured to feed the excitation light into the optical fiber via the optical contacting. Furthermore, the optical fiber may have the, in particular light-emitting, end area, which is configured for emitting the excitation light. Advantageously, the optical fiber may be arranged at least partly in the hollow needle. The light source may be arranged at least partly inside and/or outside the hollow needle. In particular, the light source may be arranged in the instrument channel. Furthermore, the hollow needle may be configured to bring out the end area of the optical fiber via the opening on the tipped section of the hollow needle into the punctured tissue, in particular the further hollow organ. Through this, an illumination of the further hollow organ, in particular of the fluid arranged therein, with the excitation light may advantageously be made possible.

The proposed form of embodiment makes possible an especially space-saving form of embodiment of the light emission unit, wherein the excitation light may be emitted via the end area of the optical fiber.

In a further advantageous form of embodiment of the proposed apparatus, the ultrasound transducer, in particular the at least one transducer element, may further be configured to emit further ultrasound and to receive the further ultrasound after an interaction with the examination region Advantageously, the ultrasound transducer may be configured for, in particular gated, emission of the further ultrasound and/or receipt of the ultrasound and/or of the further ultrasound. The ultrasound transducer may be configured to emit the further ultrasound including a predefined ultrasound signal and in particular to detect a reflected component of the further ultrasound, in particular after the interaction with the examination region of the examination object.

The proposed apparatus makes possible improved imaging of the examination region, which may advantageously be expanded by the emission and receipt of the further ultrasound. In particular, further tissue and/or fluids of the examination region may be detected by the further ultrasound, in particular mapped, which are not excitable or are only slightly excitable by the excitation light for optoacoustic emission.

In a further advantageous form of embodiment of the proposed apparatus, the apparatus may further be configured to reconstruct a spatially resolved dataset from the received ultrasound. In this case, the received ultrasound may advantageously include the ultrasound generated by the optoacoustic emission, in particular the optoacoustic waves, and/or the reflected component of the further ultrasound, in particular after the interaction with the examination region of the examination object. In particular, the ultrasound transducer may be configured to provide the signal as a function of the received ultrasound spatially resolved and/or temporally resolved. In this case, the apparatus may be configured to reconstruct the spatially resolved dataset based on the spatially resolved and/or temporally resolved signal of the ultrasound transducer.

The dataset may advantageously have a one-dimensional and/or two-dimensional and/or three-dimensional spatially resolved image of the examination region. Moreover, the dataset may be temporally resolved.

As an alternative, or in addition, the apparatus may be configured to detect and provide the spatial positioning, in particular a spatial position and/or alignment of the distal section with regard to the examination object, in particular temporally resolved. For this, the medical apparatus may advantageously have a positioning sensor, (e.g., a gyroscope and/or an electromagnetic sensor), which is configured to detect the spatial positioning of the distal section. As an alternative, or in addition, the medical apparatus may be configured to receive information about the spatial positioning of the distal section from an external detection unit, e.g., an electromagnetic and/or ultrasound-based positioning system and/or a medical imaging device. Furthermore, the ultrasound transducer may be configured to provide the signal time-resolved as a function of the received ultrasound. In this case, the medical apparatus may further be configured to correlate the time-resolved signal of the ultrasound transducer with the spatial positioning of the distal section. This enables the reconstruction of the spatially resolved dataset advantageously to be made possible.

Provided the received ultrasound includes both the ultrasound generated by the optoacoustic emission and also the reflected component of the further ultrasound, (e.g., after the interaction with examination region of the examination object), an improved reconstruction of the spatially resolved dataset may advantageously be made possible. This may be made possible by the detection, in particular imaging, of further tissue and/or fluids by the further ultrasound.

In a further advantageous form of embodiment of the proposed apparatus, the apparatus may further be configured to receive a pre-operative image dataset of the examination object. In this case, the pre-operative image dataset may have an image of the examination region. Moreover, the apparatus may be configured to register the dataset with the pre-operative image dataset. Furthermore, the apparatus may have a display unit configured to show a graphical representation of the pre-operative image dataset and of the dataset that are registered with one another.

The apparatus may further be configured to position the distal section in the examination region based on the pre-operative image dataset.

The receipt of the pre-operative image dataset may include an acquisition and and/or readout of a computer-readable data memory and/or a receipt for a data memory unit, e.g., a database. The pre-operative image dataset may further be provided by a provision unit of a medical imaging device for accepting and/or for providing the pre-operative image dataset. The medical imaging device may include one or more of a Magnetic Resonance Tomograph (MRT), a Computed Tomography system (CT), a medical x-ray device, (e.g., a medical C-arm x-ray device), an ultrasound device, or a Positron Emission Tomography system (PET).

Advantageously, the pre-operative image dataset may map the examination region pre-operatively. The pre-operative image dataset may advantageously have a two-dimensional and/or three-dimensional image of the examination region. Moreover, the pre-operative image dataset may be temporally resolved. In particular, the pre-operative image dataset may be recorded by a Magnetic Resonance Cholangio-Pancreatography (MRCP).

Advantageously, the dataset and the pre-operative image dataset at least partly map a common section of the examination region. In this case, the apparatus may further be configured to register the dataset with the pre-operative image dataset. The registration may be done here, e.g., with the aid of geometrical and/or anatomical features of the examination region. As an alternative, or in addition, the apparatus may be configured to determine the spatial positioning of the distal section, in particular, at the time of receipt of the ultrasound, with regard to the pre-operative image dataset and/or to register it with the latter. The registration of the dataset with the pre-operative image data may include a rigid and/or non-rigid transformation, (e.g., a translation and/or rotation and/or scaling), of the dataset and/or of the pre-operative image dataset.

The apparatus may further be configured to create the graphical representation by an, in particular weighted, overlaying and/or averaging of the dataset with the pre-operative image dataset. Furthermore, the display unit may be configured to show the graphical display of the dataset and of the pre-operative image dataset, which are registered with one another. In this case, the display unit may include a display and/or a monitor, for example. The display unit may further be configured to display an augmented reality (AR) and/or virtual reality (VR). The display unit may be configured, e.g., as data eyeglasses and/or a data headset and/or projector. The graphical representation may advantageously have information about alignment of bile ducts of the examination object, in particular, at that moment.

This enables an improved supervision of the puncturing by the medical apparatus and/or a navigation of the medical apparatus based on the pre-operative image dataset and the dataset to be made possible.

In a further advantageous form of embodiment of the proposed apparatus, one or more of the hollow needle, the light emission unit, or the ultrasound transducer may be movable and/or deformable. The apparatus may further be configured to control a movement and/or deformation of the hollow needle, the light emission unit, the ultrasound transducer, or a combination thereof as a function of the dataset.

The hollow needle and/or the light emission unit, (e.g., the light source and/or the optical fiber), and/or the ultrasound transducer, (e.g., the at least one transducer element), may advantageously be movable relative to one another and/or with regard to the instrument channel. The hollow needle and/or the light emission unit and/or the ultrasound transducer may further be deformable, in particular outside of the instrument channel. In this case, the apparatus may be configured to control and/or to configure a spatial positioning, (e.g., a spatial position and/or alignment and/or pose), of the hollow needle and/or of the light emission unit and/or of the ultrasound transducer, in particular mechanically, (e.g., by a control cable), and/or pneumatically and/or electromagnetically. As an alternative, or in addition, the hollow needle and/or the light emission unit and/or the ultrasound transducer may have a preformed section, which is movable, in particular positionable, after it has been brought out of the instrument channel via the opening on the distal section.

The apparatus may further be configured to control the movement and/or deformation of the hollow needle and/or of the light emission unit and/or of the ultrasound transducer as a function of the dataset. In particular, the apparatus may be configured to position the hollow needle and/or the light emission unit and/or the ultrasound transducer in the examination region as a function of the dataset. For example, the apparatus may be configured to position the instrument channel, (e.g., the distal section), in the examination region based on the pre-operative image dataset. The apparatus may further be configured to localize the puncturing point in the examination region with the aid of the dataset. Furthermore, the apparatus may be configured to control the movement and/or deformation of the hollow needle and/or of the light emission unit and/or of the ultrasound transducer, in particular, after the puncturing of the tissue, in such a way that the hollow needle and/or the light emission unit and/or the ultrasound transducer follow a spatial course of the punctured tissue, in particular of the further hollow organ.

Advantageously, the apparatus may be configured to move and/or to deform the hollow needle and/or the light emission unit and/or the ultrasound transducer in a coordinated manner and/or independently of one another.

This advantageously enables a movement and/or positioning of the medical apparatus, in particular of the hollow needle and/or of the light emission unit and/or of the ultrasound transducer, that is especially flexible and at the same time is configured to anatomical circumstances of the examination object, to be made possible.

In a further advantageous form of embodiment of the proposed apparatus, the ultrasound transducer may have a one-dimensional (1D) or two-dimensional (2D) array of transducer elements. Advantageously, the ultrasound transducer may have a number of transducer elements, which may be arranged in a spatial arrangement as a 1D array or 2D array, in particular, as grid and/or concentrically. This advantageously enables a temporally and spatially resolved receipt of the ultrasound by the ultrasound transducer to be made possible. In this case, the number of transducer elements may be arranged, e.g., in a common plane and/or along a curved surface. This advantageously enables a spatial detection area of the ultrasound transducer to be expanded.

In a further advantageous form of embodiment of the proposed apparatus, the ultrasound transducer may have an annular opening to accommodate the hollow needle. In this case, the hollow needle may be arranged at least partly in the annular opening. In particular, the hollow needle and the light emission unit arranged at least partly therein may be arranged at least partly in the annular opening of the ultrasound transducer. Advantageously, the ultrasound transducer may surround the hollow needle in an annular shape, in particular in the form of a sheath. The ultrasound transducer may further be configured to be moved out via the opening on the distal section of the instrument channel. Moreover, the hollow needle may be movable with regard to the ultrasound transducer in such a way that the hollow needle may puncture the tissue through the annular opening. Advantageously, the ultrasound transducer is configured to be arranged at the puncturing point. In this case, the ultrasound transducer, in particular the at least one transducer element, may advantageously acoustically contact the punctured tissue. For this, the ultrasound transducer may be brought into tissue contact with the tissue to be punctured and/or the puncturing point and/or the hollow organ. If the ultrasound transducer has a number of transducer elements, which may be arranged as a 1D array or 2D array, the transducer elements may be arranged, (e.g., concentrically), around the annular opening for accommodating the hollow needle.

This enables an, in particular direct, arrangement of the ultrasound transducer at the puncturing point to be made possible.

In a further advantageous form of embodiment of the proposed apparatus, the ultrasound transducer may be coupled mechanically moveably to the instrument channel or may be arranged in a fixed position with regard to the instrument channel.

In this case, the ultrasound transducer may advantageously be arranged on an outer side of the instrument channel, in particular on the distal section. The ultrasound transducer may further be coupled mechanically movably to the instrument channel in such a way that the ultrasound transducer is rotatable and/or tiltable with regard to the instrument channel. As an alternative, the ultrasound transducer may be arranged in a fixed position with regard to the instrument channel. Advantageously, the ultrasound transducer may be arranged on the instrument channel in such a way that a detection area of the ultrasound transducer at least partly includes the hollow needle and/or the light emission unit after they have been brought out from the opening of the instrument channel.

This enables an especially flexible spatial arrangement, in particular alignment, of the ultrasound transducer to be made possible.

In a further advantageous form of embodiment of the proposed apparatus, the excitation light may be configured to excite a first fluorescence dye for optoacoustic emission of ultrasound. Advantageously, the light emission unit, (e.g., the light source), may be configured to generate the excitation light in such a way that the first fluorescence dye for optoacoustic emission of ultrasound may be excited in the examination region. In particular, the light emission unit may be configured to generate the excitation light with a defined wavelength and/or within a defined wavelength range, wherein the defined wavelength and/or the defined wavelength range at least partly matches an absorption spectrum, in particular an absorption wavelength and/or an absorption wavelength range, of the first fluorescence dye.

The excitation of the first fluorescence dye by the light emission unit advantageously enables a stronger optoacoustic emission in the punctured tissue, in particular the further hollow organ, to be achieved. This enables a better signal-to-noise ratio (SNR) in the ultrasound received by the ultrasound transducer to be achieved. Furthermore, by the excitation light, an explicit excitation of the first fluorescence dye for optoacoustic emission and only slight or no excitation of further tissue and/or fluids may advantageously be insured.

In a further advantageous form of embodiment of the proposed apparatus, the apparatus may furthermore have an optical sensor. In this case, the excitation light may advantageously further be configured to excite an emission of fluorescent light. Moreover, the optical sensor may be configured to receive the fluorescent light.

Advantageously, the light emission unit, (e.g., the light source), may be configured to generate the excitation light in such a way that a tissue of the examination region, (e.g., the punctured tissue), and/or the hollow organ and/or the further hollow organ, and/or a fluid, (e.g., a bodily fluid and/or a contrast medium), is excited for emission of fluorescent light. In particular, the light emission unit may be configured to generate the excitation light with a defined wavelength and/or within a defined wavelength range, wherein the defined wavelength and/or the defined wavelength range at least partly matches an absorption spectrum, (e.g., an absorption wavelength and/or an absorption wavelength range), of the tissue and/or fluid to be excited.

Advantageously, the optical sensor may have a photocell and/or a camera sensor and/or a photomultiplier tube, (PMT), which is configured for, in particular spatially and/or temporally resolved, detection of the fluorescent light. The optical sensor may advantageously be arranged on the distal section of the apparatus, in particular on an outer side of the instrument channel. The optical sensor may further be coupled mechanically movably to the instrument channel in such a way that the optical sensor is rotatable and/or tiltable with regard to the instrument channel. As an alternative, the optical sensor may be arranged in a fixed location with regard to the instrument channel. Advantageously, the optical sensor may be arranged on the instrument channel in such a way that a detection area of the optical sensor at least partly includes the hollow needle and/or the light emission unit after they have been brought out of the opening of the instrument channel. Furthermore, the optical sensor may be arranged on the ultrasound transducer and/or on the hollow needle.

Moreover, the apparatus may be configured additionally to reconstruct the spatially resolved dataset from the received fluorescent light. The proposed form of embodiment advantageously makes possible improved imaging, in particular hybrid imaging, of the examination region. Furthermore, the ultrasound transducer and the optical sensor may have at least partly overlapping and/or different detection areas, whereby a comprehensive sampling of the examination region may be made possible. In particular, the ultrasound transducer and the optical sensor may be configured for simultaneous and/or independent receipt of the ultrasound or of the fluorescent light.

In a further advantageous form of embodiment of the proposed apparatus, the optical fiber may additionally contact the optical sensor. In this case, the end area of the optical fiber may further be configured for receiving the fluorescent light.

Advantageously, the optical fiber may optically contact both the light source and also the optical sensor. In this case, the optical fiber, in particular the end area of the optical fiber, may be configured bidirectional for emission of the excitation light and for receipt of the fluorescent light. Advantageously, the optical sensor and/or the light emission unit may further have an, in particular optical, filter for filtering the received fluorescent light, which may be arranged, e.g., between the optical fiber and the optical sensor. In this case, the optical sensor may be arranged on a proximal end area of the medical apparatus and/or within the instrument channel and/or within the hollow needle.

This advantageously enables the fluorescent light also to be received in the punctured tissue, in particular, the further hollow organ. The proposed form of embodiment further makes possible an especially space-saving version of the proposed apparatus.

In a further advantageous form of embodiment of the proposed apparatus, the excitation light may be configured to excite a first and/or a second fluorescence dye in each case for optoacoustic emission of ultrasound and/or for emission of fluorescent light.

In this case, the excitation light may be configured, e.g., to excite the first fluorescence dye for optoacoustic emission of ultrasound and the second fluorescence dye for emission of fluorescent light. In this case, the first and the second fluorescence dye may advantageously be arranged in at least partly different regions, in particular, tissues and/or hollow organs, of the examination region. This enables an imaging of the at least partly different regions to be made possible with the aid of the received fluorescent light and the received ultrasound.

The excitation light may further be configured, e.g., to excite the first fluorescence dye and/or the second fluorescence dye in each case for optoacoustic emission of ultrasound and for emission of fluorescent light. In this case, the ultrasound generated and/or the fluorescent light generated may advantageously differ at least partly between the first and the second fluorescence dye, e.g., in respect of a wavelength and/or a wavelength range.

Furthermore, the excitation light may be configured to excite only the first or only the second fluorescence dye, in particular selectively, for optoacoustic emission of ultrasound and/or for emission of fluorescent light.

The proposed form of embodiment enables an improved, in particular dedicated, detection of the first and/or of the second fluorescence dye to be made possible by the received ultrasound and/or of the received fluorescent light.

In a further advantageous form of embodiment of the proposed apparatus, the light emission unit and/or ultrasound transducer may be movable in relation to the instrument channel. In this case, the apparatus may be configured to carry out a predefined movement of the light emission unit and/or of the ultrasound transducer. Moreover, the apparatus may be configured to reconstruct a spatial distribution of the received ultrasound based on a tomography algorithm.

Advantageously, the light emission unit, (e.g., the light source and/or the optical fiber), and/or the ultrasound transducer may be movable, (e.g., rotatable and/or tiltable and/or translatable and/or deformable), in relation to the instrument channel. The apparatus may be configured to control and/or to adapt the predefined movement of the light emission unit, (e.g., of the light source and/or of the optical fiber), and/or of the ultrasound transducer, in particular mechanically, (e.g., by a control cable), and/or pneumatically and/or electromagnetically. In particular, the apparatus may be configured to move the light emission unit and/or the ultrasound transducer in a defined manner in such a way that the light emission unit and/or the ultrasound transducer, at least in sections, have a predefined spatial positioning, in particular position and/or alignment and/or pose. The apparatus may further be configured to arrange the light emission unit and/or the ultrasound transducer in accordance with a predetermined trajectory with regard to the instrument channel. In this case, the predetermined trajectory may have a temporal sequence of predefined spatial positionings of the light emission unit and/or of the ultrasound transducer. In particular, the apparatus may be configured to arrange the light emission unit and/or the ultrasound transducer in the temporal sequence of predefined spatial positionings with regard to the instrument channel.

The apparatus may moreover be configured to move the light emission unit and/or the ultrasound transducer in such a way that a predetermined spatial segment of the examination region, (e.g., of the punctured tissue), may be illuminated with the excitation light and/or scanned by the ultrasound transducer. Where the ultrasound transducer has a 1D or 2D array of transducer elements, the apparatus may be configured to move the 1D or 2D array of transducer elements in such a way that the ultrasound of a 3D volume of the examination region, (e.g., of the punctured tissue), may be received by the 1D or 2D arrays of transducer elements. The ultrasound transducer, in particular the 1D or 2D array of transducer elements, may further be configured to provide the signal additionally spatially resolved as a function of the received ultrasound. In this case, the signal may advantageously be spatially resolved at least with regard to the number of transducer elements of the ultrasound transducer, in particular of the 1D or 2D arrays. The apparatus, in particular the ultrasound transducer, may further be configured in each case to provide a part signal as a function of the ultrasound received in the respective spatial positioning of the light emission unit and/or of the ultrasound transducer with regard to the instrument channel. The apparatus may further be configured to reconstruct a spatial distribution of the ultrasound received by the ultrasound transducer by application of a tomography algorithm to the part signals, in particular as a function the predefined movement of the light emission unit and/or of the ultrasound transducer.

In this case, the apparatus may be configured to reconstruct a number of individual images, (e.g., one-dimensional (1D) and/or two-dimensional (2D) and/or three-dimensional (3D) individual images), from the part signals of the ultrasound transducer. In this case, the individual images may advantageously each map at least a part of the examination region. The individual images may further at least partly map spatially adjoining and/or overlapping segments of the examination region. The apparatus may further be configured to reconstruct a volume image of the examination region with the aid of the spatial distribution of the ultrasound received by the ultrasound transducer and/or with the aid of the individual images.

This enables an improved spatial navigation, in particular orientation, of the medical apparatus in the examination region, in particular for puncturing, to be made possible.

In a second aspect, the disclosure relates to a system having a processing unit, a movement apparatus, and a medical apparatus. In this case, the apparatus has a light emission unit and a receive unit. Moreover, the apparatus is configured to be arranged at least partly in an examination region of an examination object. The light emission unit is further configured for emission of excitation light. In this case, the excitation light is configured to excite an optoacoustic emission of ultrasound and/or an emission of fluorescent light. Furthermore, the receive unit and the light emission unit are arranged on a distal section of the apparatus. Moreover, the receive unit is configured for receiving the ultrasound and/or of the fluorescent light. The receive unit is further configured for provision of a signal to the processing unit as a function of the received ultrasound and/or of the received fluorescent light. Moreover, the movement apparatus is configured for robotic movement of the apparatus. The processing unit is further configured to provide a control signal for control of the movement of the apparatus by the movement apparatus based on the signal.

The advantages of the proposed system correspond to the advantages of the proposed medical apparatus. Features, advantages, or alternate forms of embodiment mentioned here may likewise be transferred to the other claimed subject matter and vice versa. The medical apparatus and/or the light emission unit and/or the examination object and/or the excitation light may in particular have all characteristics and features that have been described with regard to the medical apparatus and vice versa.

Advantageously, the movement apparatus may be a robotic apparatus configured for remote manipulation of the medical apparatus, e.g., a catheter robot. The movement apparatus may further be arranged outside of the examination object. Furthermore, the movement apparatus may have an, in particular movable and/or drivable, attachment element. Moreover, the movement apparatus may have a cassette element configured to accommodate at least a part of the medical apparatus. Furthermore, the movement apparatus may have a movement element fastened to the attachment element, e.g., a stand and/or robot arm. Moreover, the attachment element may be configured to attach the movement element to a patient support apparatus. The movement element may further advantageously have at least one actuator element, e.g., an electric motor, wherein the processing unit is configured to control the actuator element. Advantageously, the cassette element may be coupled, (e.g., mechanically and/or electromagnetically and/or pneumatically), to the movement element, in particular to the at least one actuator element. In this case, the cassette element may further have at least one transmission element, which is movable by the coupling between the cassette element and the movement element, in particular the at least one actuator element. In particular, the at least one transmission element may be coupled for movement to the at least one actuator element. Advantageously, the transmission element is configured to transmit a movement, in particular the force, of the actuator element to the medical apparatus in such a way that the medical apparatus is moved in a longitudinal direction of the medical apparatus and/or the medical apparatus is rotated about its own longitudinal direction. The at least one transmission element may have a pulley and/or roller and/or metal plate and/or shear plate.

Advantageously, the movement element may have a number of, in particular independently controllable, actuator elements. The cassette element may further have a number of transmission elements, in particular at least one movement-coupled transmission element for each of the actuator elements. This enables an, in particular independent and/or simultaneous, movement of the medical apparatus along various degrees of freedom of movement to be made possible.

Advantageously, the light emission unit and/or the receive unit may be arranged on a distal section of the medical apparatus. In this case, the receive unit may advantageously be arranged aligned forwards and/or aligned sideways with regard to the longitudinal direction of medical apparatus on the distal section. Furthermore, the movement apparatus may be configured to position the distal section in the examination region, in particular, at a predetermined spatial position and/or in a predetermined alignment and/or pose. In particular, the movement apparatus may be configured to deform the medical apparatus at least in sections, e.g., by a control cable, and/or pneumatically and/or electromagnetically.

The processing unit may advantageously be configured to provide the control signal for controlling the movement of the medical apparatus by the movement apparatus based on the signal. In this case, the movement apparatus may be configured to move the medical apparatus as a function of the control signal of the processing unit. In particular, the movement apparatus may be configured to move and/or to position the distal section of the medical apparatus as a function of the control signal. Advantageously, the processing unit may be configured to provide the control signal as a function of an intensity, in particular of a spatial intensity distribution, of the signal. This enables the movement apparatus to be configured to navigate the medical apparatus, in particular, the distal section, as a function of the intensity of the signal, in particular of the received ultrasound and/or of the received fluorescent light. Advantageously, the medical apparatus is configured to be arranged and/or moved at least partly in a hollow organ of the examination object. The processing unit may further be configured to localize a further hollow organ, which adjoins the hollow organ, e.g., a bile duct, with the aid of the received ultrasound and/or of the received fluorescent light. As an alternative, or in addition, the processing unit may be configured to reconstruct the spatial course of the hollow organ, in particular along a direction of movement of the medical apparatus, with the aid of the received ultrasound and/or with the aid of the received fluorescent light. In particular, the movement apparatus may be configured to adapt and/or to stop a movement of the medical apparatus when the control signal changes.

This advantageously enables an improved movement, in particular navigation, of the medical apparatus by the movement apparatus to be made possible. Moreover, a risk of injury for the examination object may advantageously be reduced.

In a further advantageous form of embodiment of the proposed system, the receive unit may have an ultrasound transducer configured for receiving the ultrasound.

The ultrasound transducer may have all characteristics and features that have been described with regard to the medical apparatus and vice versa. In particular, the ultrasound transducer may have at least one transducer element configured for detection of the ultrasound.

In a further advantageous form of embodiment of the proposed system, the ultrasound transducer, in particular the at least one transducer element, may further be configured to emit further ultrasound and to receive the further ultrasound after an interaction with the examination region.

Advantageously, the ultrasound transducer may be configured for gated emission of the further ultrasound and/or receipt of the ultrasound and/or of the further ultrasound. The ultrasound transducer may be configured to emit the further ultrasound including a predefined ultrasound signal and to receive, in particular to detect, a reflected component of the further ultrasound, in particular after the interaction with the examination region of the examination object.

The proposed system makes possible an improved imaging of the examination region, which may advantageously be expanded by emission and receipt of the further ultrasound. In particular, further tissue and/or fluids of the examination region, which are not excitable or are only slightly excitable by the excitation light for optoacoustic emission are detected, in particular imaged, by the further ultrasound.

In a further advantageous form of embodiment of the proposed system, the receive unit may have an optical sensor configured to receive the fluorescent light. In this case, the optical sensor may have a photocell and/or a camera sensor and/or a photomultiplier tube (PMT), which is configured for, in particular spatially and/or temporally resolved, detection of the fluorescent light.

The medical apparatus may have the ultrasound transducer and the optical sensor. This enables improved imaging, in particular hybrid imaging, of the examination region to be made possible. Furthermore, the ultrasound transducer and the optical sensor may have at least partly overlapping or different detection areas, whereby a comprehensive scanning of the examination region may be made possible. In particular, the ultrasound transducer and the optical sensor may be configured for simultaneous and/or independent receipt of the ultrasound or of the fluorescent light.

In a further advantageous form of embodiment of the system, the excitation light may be configured to excite a first and/or a second fluorescence dye in each case for optoacoustic emission of ultrasound and/or for emission of fluorescent light.

Advantageously, the light emission unit, (e.g., the light source), may be configured to generate the excitation light in such a way that a first and/or second fluorescence dye arranged in the examination region is excited, in particular selectively, for optoacoustic emission of ultrasound and/or for emission of fluorescent light. In particular, the light emission unit may be configured to generate the excitation light with a defined wavelength and/or within a defined wavelength range, wherein the defined wavelength and/or the defined wavelength range at least partly matches an absorption spectrum, (e.g., an absorption wavelength and/or an absorption wavelength range), of the first and/or of the second fluorescence dye. In particular, the excitation light may have a narrowband and/or wideband wavelength range, e.g., in an infrared range and/or near infrared range. Furthermore the excitation light may be configured multispectrally.

In this case, the first and the second fluorescence dye may advantageously be arranged in at least partly different regions, in particular tissues and/or hollow organs, of the examination region. This enables imaging of the at least partly different regions to be made possible with the aid of the received fluorescent light and/or of the received ultrasound. As an alternative, or in addition, the excitation light may be configured to excite the first fluorescence dye and/or the second fluorescence dye in each case for optoacoustic emission of ultrasound and for emission of fluorescent light. The ultrasound generated in this case and/or the fluorescent light generated may advantageously distinguish at least partly between the first and the second fluorescence dye, e.g., in respect of a wavelength and/or of a wavelength range. This enables an improved, in particular dedicated, detection of the first and/or of the second fluorescence dye to be made possible by the received ultrasound and/or of the received fluorescent light.

Advantageously, the first and/or the second fluorescence dye may be arranged in the hollow organ and/or the further hollow organ and/or in adjoining tissue. The excitation of the first and/or of the second fluorescence dye by the light emission unit advantageously enables a stronger optoacoustic emission in the punctured tissue, in particular the further hollow organ, to be achieved. This enables a better signal-to-noise ratio (SNR) for the ultrasound received by the ultrasound transducer to be achieved.

Furthermore, an explicit excitation of the first and/or of the second fluorescence dye for optoacoustic emission of ultrasound and/or for emission of fluorescent light may advantageously be insured by the excitation light.

In a further advantageous form of embodiment of the proposed system, the medical apparatus may be a proposed apparatus. In this case, the medical apparatus may have all characteristics and features that have been described with regard to the proposed medical apparatus.

BRIEF DESCRIPTION OF THE DRAWINGS

Exemplary embodiments of the disclosure are shown in the drawings and will be described in greater detail below. In different figures, the same reference characters are used for the same features. In the figures.

DETAILED DESCRIPTION

Figure 1:
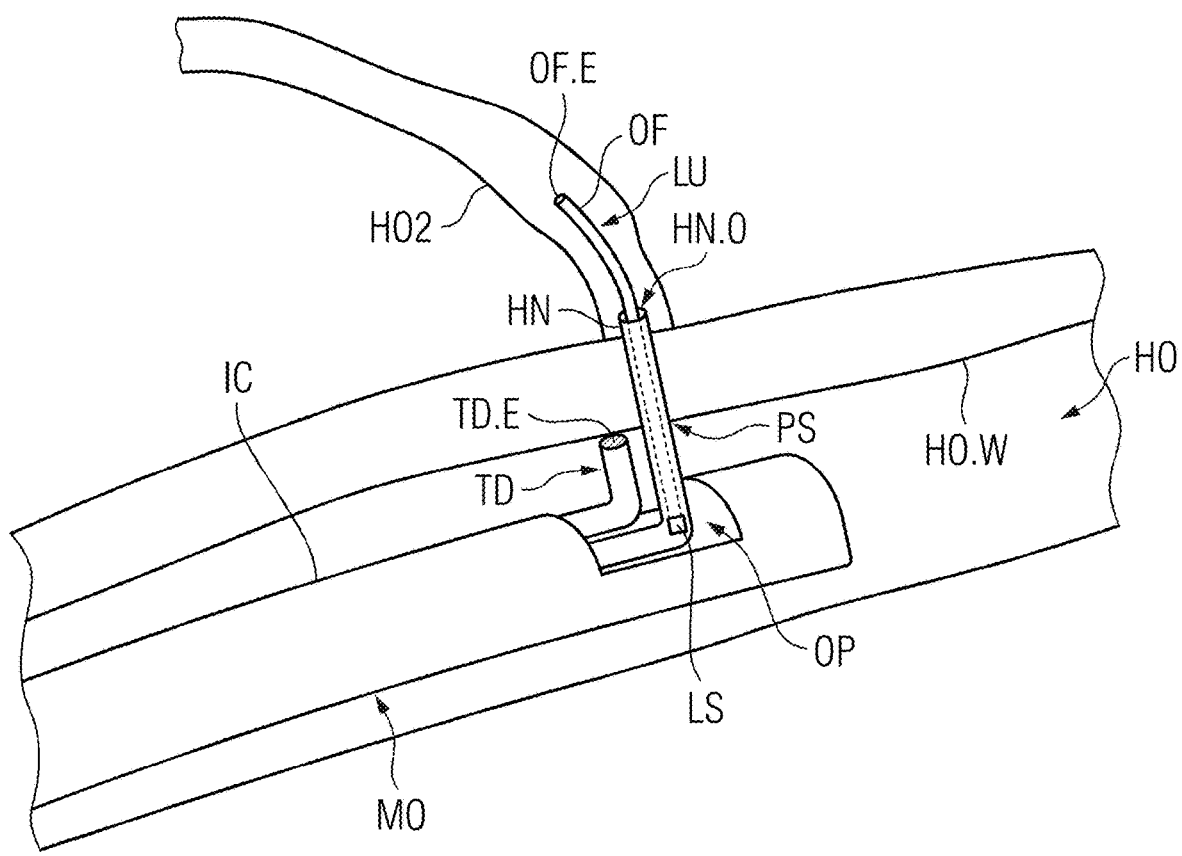
FIGS. 1 to 4 depict schematic diagrams of different forms of embodiment of a proposed medical apparatus.

Shown schematically in FIG. 1 is an advantageous form of embodiment of a proposed medical apparatus MO. The medical apparatus MO may advantageously have a light emission unit LU, an ultrasound transducer TD, an instrument channel IC, and a hollow needle HN. In this case, the apparatus MO may be configured to be arranged at least partly in an examination region such as a hollow organ HO, (e.g., a duodenum and/or a vessel section such as an artery and/or vein), of an examination object. The light emission unit LU may further be configured to emit excitation light. The excitation light may furthermore be configured to excite an optoacoustic emission of ultrasound. Moreover, the light emission unit LU may be arranged at least partly in the hollow needle HN. The hollow needle HN may further be configured to be arranged at least partly for movement in the instrument channel IC. The instrument channel IC may furthermore have an opening OP for bringing out the hollow needle HN and the light emission unit LU on a distal section of the apparatus. Moreover, the ultrasound transducer TD may be arranged on the distal section of the apparatus MO. The hollow needle HN may further be configured, for puncturing a tissue in the examination region, to be moved out at least partly through the opening OP from the instrument channel IC. The ultrasound transducer TD may furthermore be configured for receipt of the ultrasound.

The hollow needle HN may advantageously be configured rigidly and/or flexibly at least in sections. The hollow needle HN may further have a tipped section configured for puncturing of the tissue, (e.g., of a wall HO.W of the hollow organ HO). In particular, the hollow needle HN may be configured to puncture the wall HO.W of the hollow organ HO by the tipped section, at a puncturing point PS after being moved out of the opening of the instrument channel OP, in particular to break through it. Advantageously, the punctured tissue, (e.g., the punctured wall HO.W of the hollow organ HO), may surround a further hollow organ HO2, (e.g., a bile duct), wherein an, in particular bodily, fluid may be arranged in the further hollow organ HO2.

The light emission unit LU may advantageously have a light source LS, (e.g., a Light-Emitting Diode (LED) and/or a laser), which is configured to generate and/or emit the excitation light of a defined wavelength and/or of a defined wavelength range. Moreover, the light emission unit LU may have an optical fiber OF, which optically contacts the light source LS. In this case, the light source LS may be arranged on a proximal end area of the medical apparatus MO and/or within the instrument channel IC and/or within the hollow needle HN. The optical fiber OF may further have an, in particular light-emitting, end area OF.E for emitting the excitation light from the light source LS. Furthermore, the hollow needle HN may have an opening HN.O on the tipped section, wherein the hollow needle HN is configured for bringing out the end area OF.E of the optical fiber OF via the opening HN.O on the tipped section.

Furthermore, the hollow needle HN may be arranged at least partly, in particular translationally and/or rotationally, movably in the instrument channel IC. In particular, the hollow needle HN may be movable in a longitudinal direction of the medical apparatus MO translationally and/or around the longitudinal direction of the medical apparatus MO rotationally in the instrument channel IC.

The ultrasound transducer TD may advantageously have at least one transducer element TD.E configured to detect the ultrasound, (e.g., the acoustic signal of the ultrasound), in the examination region. The ultrasound transducer TD, (e.g., the at least one transducer element TD.E), may be arranged at least partly in the instrument channel IC and/or be able to be brought out via the opening OP on the distal section of the instrument channel IC. In this case, the ultrasound transducer TD, (e.g., the at least one transducer element TD.E), may acoustically contact the punctured tissue.

Moreover, the ultrasound transducer TD may be configured to emit further ultrasound and to receive the further ultrasound after an interaction with the examination region of the examination object.

Figure 2:
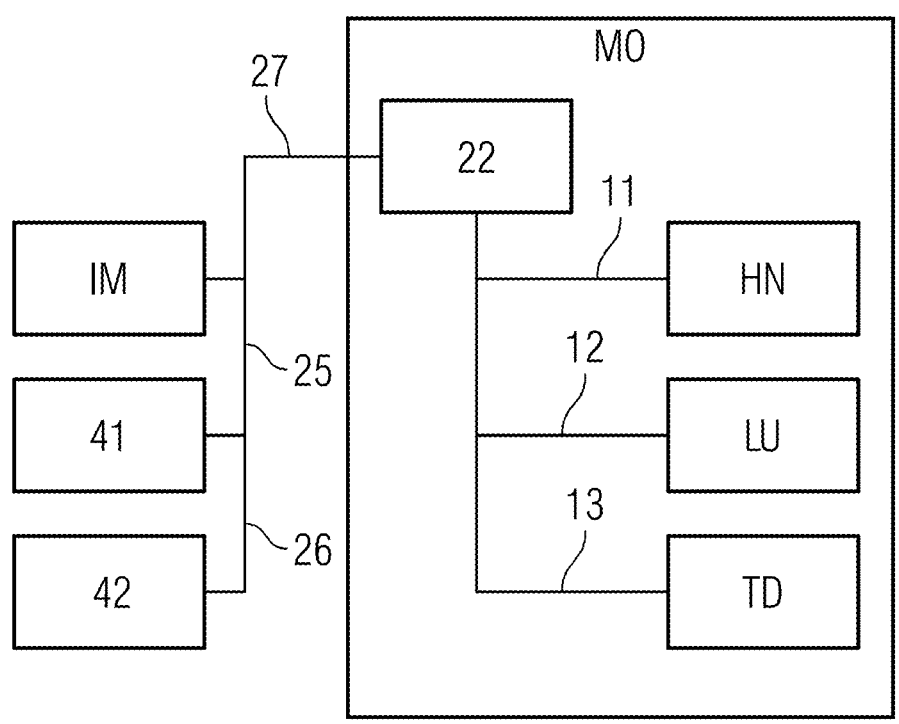

FIG. 2 shows a further advantageous form of embodiment of a proposed medical apparatus MO, wherein an interaction between different components of the medical apparatus MO is shown schematically. Advantageously, the medical apparatus MO may include a processing unit 22. Advantageously, the medical apparatus MO, in particular the processing unit 22, may be configured to reconstruct a spatially resolved dataset from the received ultrasound. For this, the ultrasound transducer TD may be configured to provide a signal 13 to the processing unit 22 as a function of the received ultrasound. The received ultrasound may advantageously include the ultrasound brought about by the optoacoustic emission, in particular the optoacoustic waves, and/or the reflected component of the further ultrasound, in particular after the interaction with the examination region of the examination object.

Moreover, the apparatus MO, in particular the processing unit 22, may be configured to segment the hollow organ HO and/or the further hollow organ HO2, in particular a bile duct, with the aid of the signal, in particular with the aid of an optoacoustic tissue contrast and/or an optoacoustic contrast between a bile fluid and a tissue.

The hollow needle HN and/or the light emission unit LU and/or the ultrasound transducer TD may further be movable and/or deformable. In this case, the apparatus MO, (e.g., the processing unit), may be configured to control a movement and/or deformation of the hollow needle HN and/or of the light emission unit LU and/or of the ultrasound transducer TD as a function of the dataset by the respective signal 11, 12 or 13. Furthermore, the medical apparatus may have an input unit 42 for detecting an input of a user. The input unit 42 may include a keyboard and/or a pointing device, in particular a computer mouse. The input unit 42 may further be configured to provide a signal 26 to the processing unit 22 as a function of the input of the user detected. This advantageously enables control of the medical apparatus MO, in particular of its components, by the user to be made possible by the input unit 42.

Furthermore, the apparatus MO, (e.g., the processing unit 22), may be configured for receiving a pre-operative image dataset of the examination object, in particular by a signal 27 from a medical imaging device IM. In this case, the pre-operative image dataset may have an image of the examination object. Moreover, the apparatus MO may be configured to register the dataset with the pre-operative image dataset.

The apparatus MO may further have a display unit 41 configured to show a graphical display of the pre-operative image dataset and the dataset, which are registered with one another. For this, the processing unit 22 may send a signal 25 to the display unit 41. The display unit 41 may advantageously have a monitor and/or a display. The input unit 42 may further be integrated at least partly in the display unit 41, e.g., with a capacitive and/or resistive input display.

Figure 3:
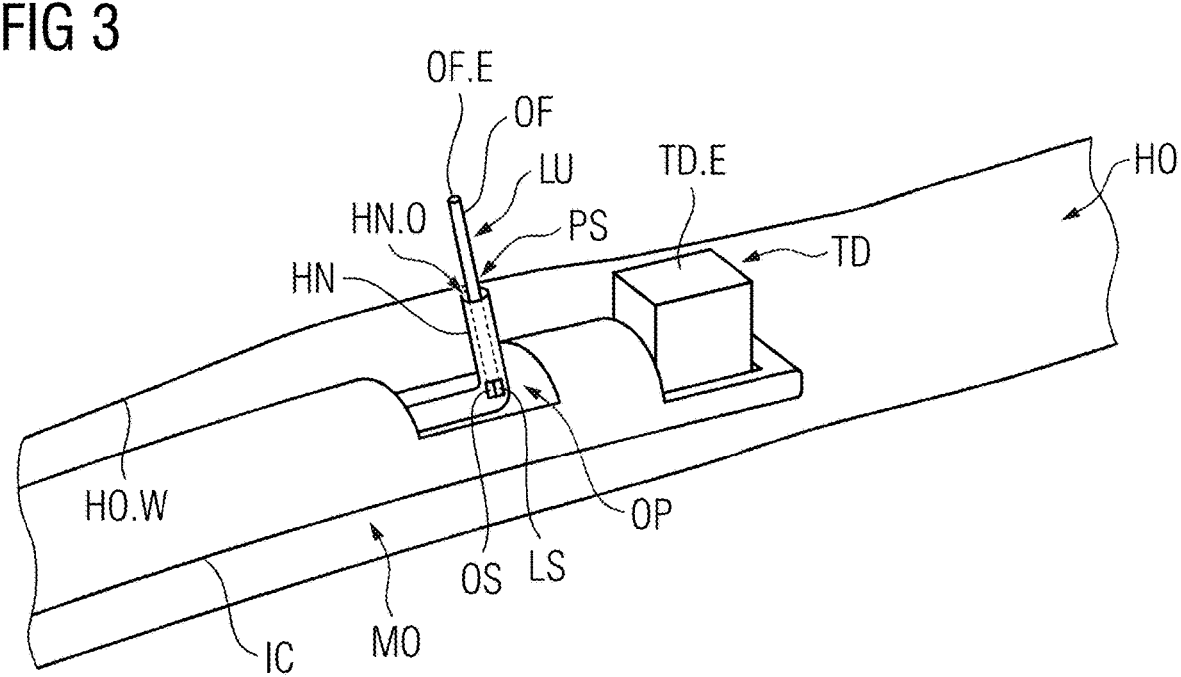

FIG. 3 shows a further advantageous form of embodiment of a proposed medical apparatus MO, wherein the ultrasound transducer TD, in particular the at least one transducer element TD.E, may be arranged coupled mechanically movably to the instrument channel IC or in a fixed location with regard to the instrument channel IC. Moreover, the ultrasound transducer TD may have a 1D or 2D array of transducer elements TD.E.

Furthermore, the excitation light may be configured to excite an emission of fluorescent light. For this, the apparatus MO may have an optical sensor OS, which is configured for receiving the fluorescent light. In this case the optical fiber OF may additionally optically contact the optical sensor OS. The end area OF.E of the optical fiber OF may additionally be configured to receive the fluorescent light. Advantageously, the optical sensor OS may be configured to provide a corresponding signal to the processing unit 22 as a function of the received fluorescent light.

Figure 4:
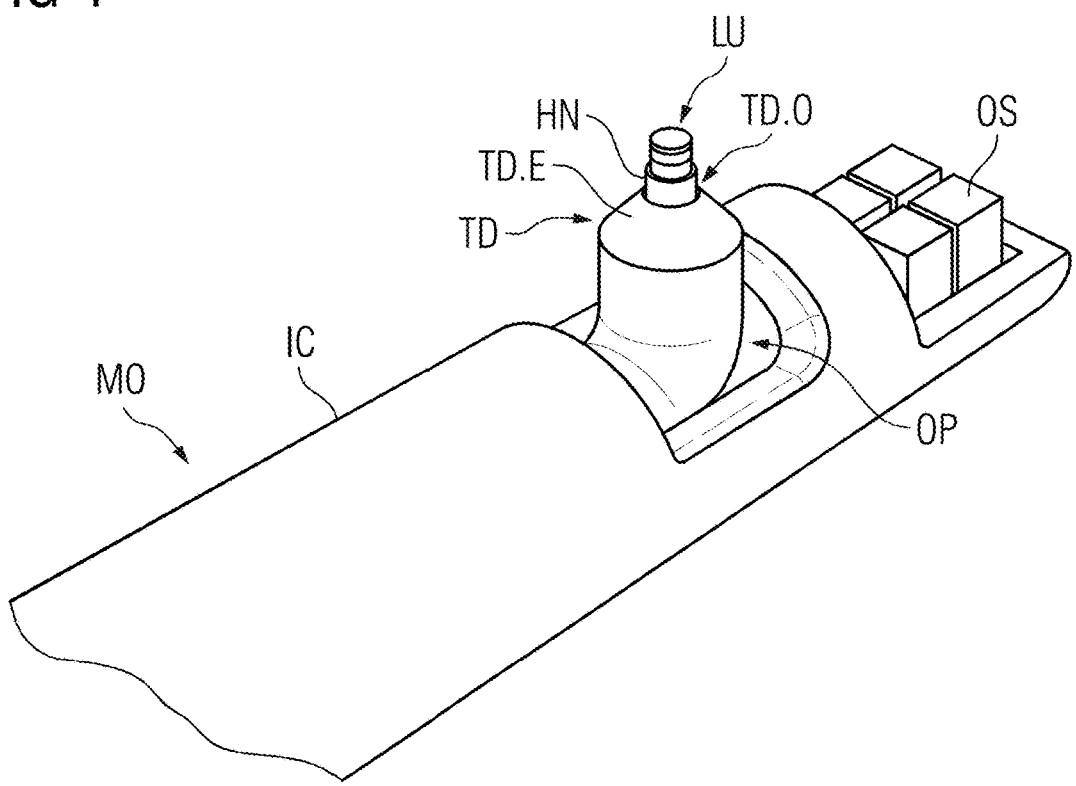

Shown schematically in FIG. 4 is a further advantageous form of embodiment of the proposed medical apparatus MO. In this case, the ultrasound transducer TD may have an annular opening TD.O to accommodate the hollow needle HN, wherein the hollow needle HN is arranged at least partly in the annular opening TD.O.

In this case, the light emission unit LU and/or the ultrasound transducer TD may be movable in relation to the instrument channel IC. The apparatus MO may further be configured to carry out a predefined movement of the light emission unit LU and/or of the ultrasound transducer TD. Furthermore, the apparatus MO may be configured to reconstruct a spatial distribution of the received ultrasound based on a tomography algorithm. Moreover, the optical sensor OS may be arranged e.g., on the distal section of the medical apparatus MO.

Figure 5:
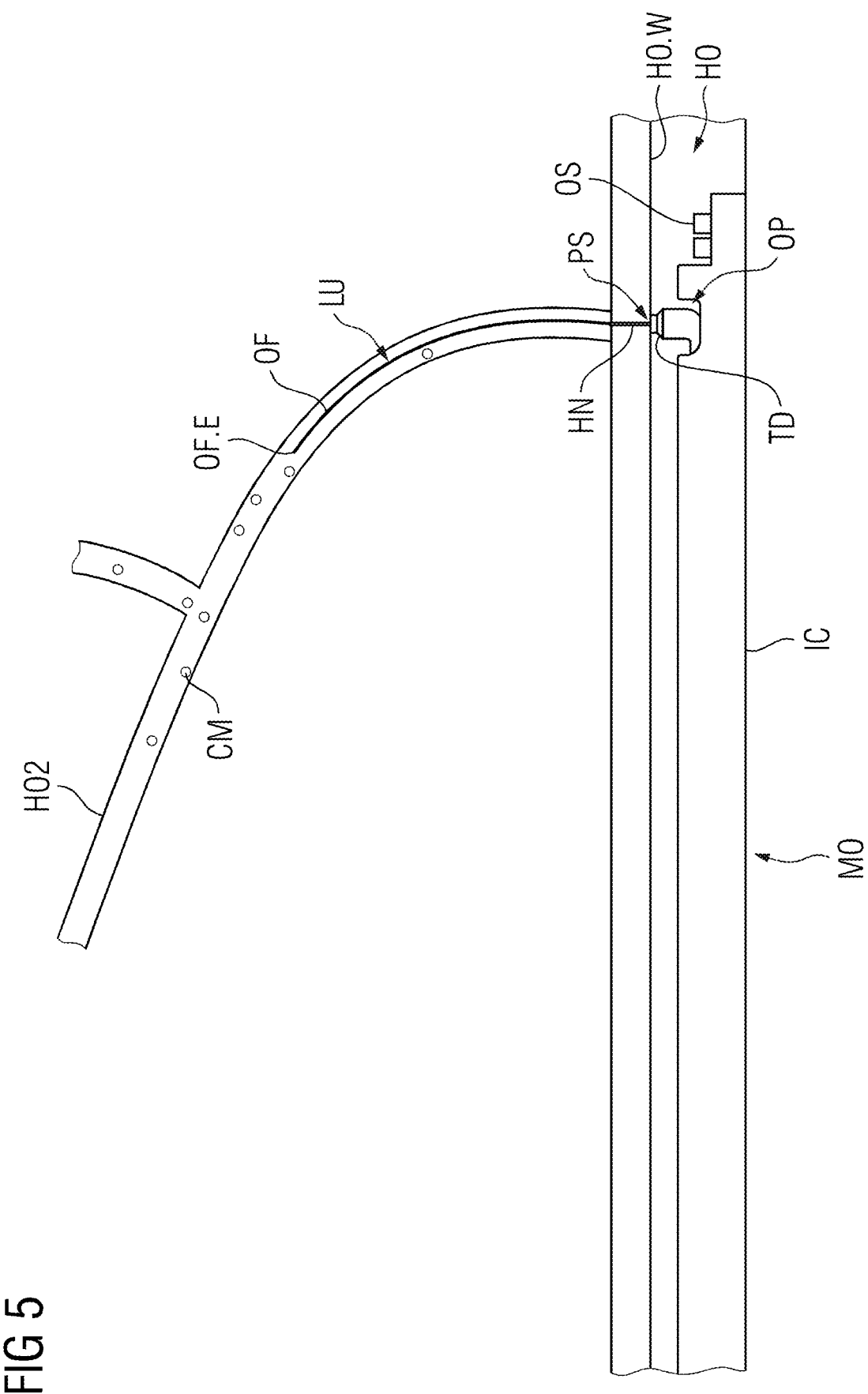
FIGS. 5 and 6 depict schematic diagrams of different application examples of a proposed medical apparatus.

FIG. 5 shows a further advantageous form of embodiment of the proposed medical apparatus MO. In the form of embodiment shown schematically in FIG. 5, the wall HO.W of the hollow organ HO may have been punctured by the tipped section of the hollow needle HN at the puncturing point PS. The optical fiber OF may further have been brought out of the hollow needle HN into the further hollow organ HO2. Moreover, a first fluorescence dye CM, (e.g., indocyanine green (ICG)), may be arranged in the further hollow organ HO2. The end area OF.E of the optical fiber OF may further be configured to emit the excitation light in the further hollow organ HO2. In this case, the excitation light may be configured to excite the first fluorescence dye CM for optoacoustic emission of ultrasound. Furthermore, the ultrasound transducer TD may acoustically contact the wall of the hollow organ HO and/or of the further hollow organ HO2 in such a way that the ultrasound transducer TD receives the ultrasound.

ICG may have a half-life value of appr. 4 to 5 minutes and is frequently exclusively secreted by a liver of the examination object. Therefore, it may be advantageous for the ICG to have been administered to the examination object systemically, in particular between 30 minutes and 1 hour before the beginning of an examination and/or puncturing that is to be carried out by the medical apparatus. This advantageously enables it to be insured that the ICG has been flushed out again from the blood circulation systems and from the tissue, wherein ICG may still be arranged in the bile ducts of the examination object, because it is frequently excreted via these bile ducts.

As an alternative, or in addition, a specific contrast medium applied to inflammations (e.g., molecular agent) may be administered. This advantageously enables a functional and/or specific and/or molecular, in particular spatially resolved, imaging, in particular of inflammatory reactions in the bile ducts, by the medical apparatus to be made possible.

In this case, the excitation light may advantageously be configured to excite the first and/or a second fluorescence dye in each case for optoacoustic emission of ultrasound and/or for emission of fluorescent light.

Figure 6:
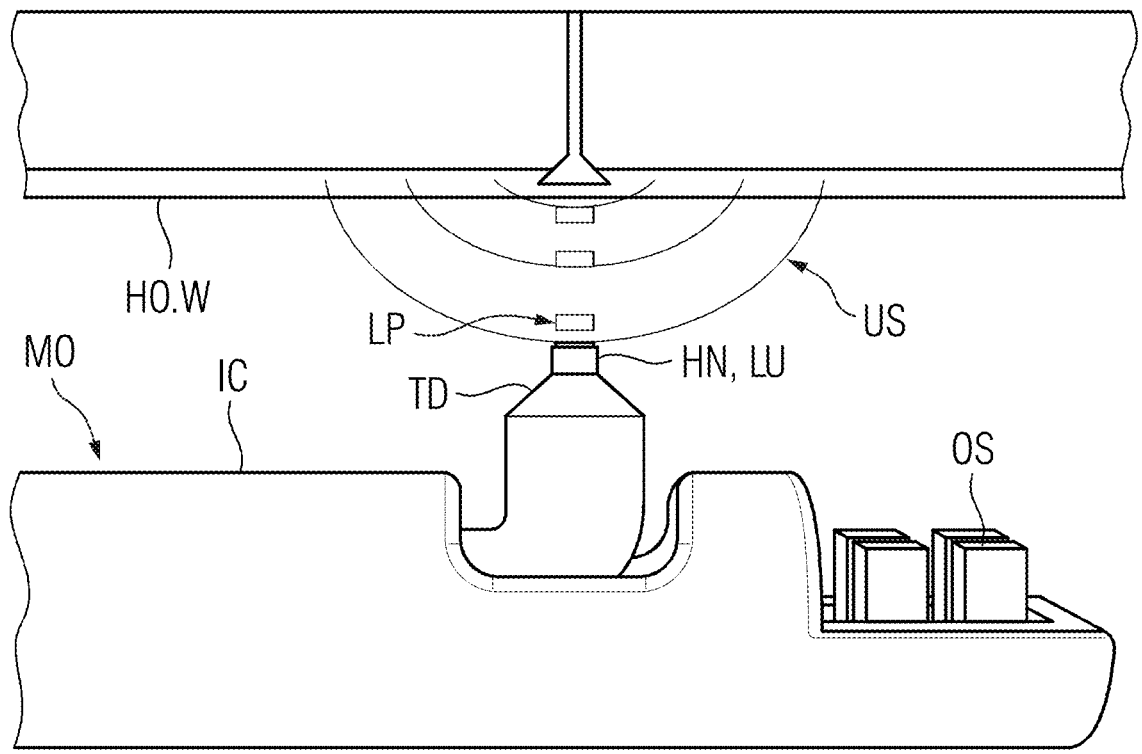

Shown schematically in FIG. 6 is a further advantageous form of embodiment of the proposed medical apparatus MO. In this case, the light emission unit LU is configured for emitting pulsed excitation light LP. The pulsed excitation light LP may further be configured to excite the tissue adjoining the hollow organ HO, in particular the wall HO.W of the hollow organ HO, for emission of ultrasound US. The ultrasound transducer TD may further be configured for receiving the ultrasound US.

Figure 7:
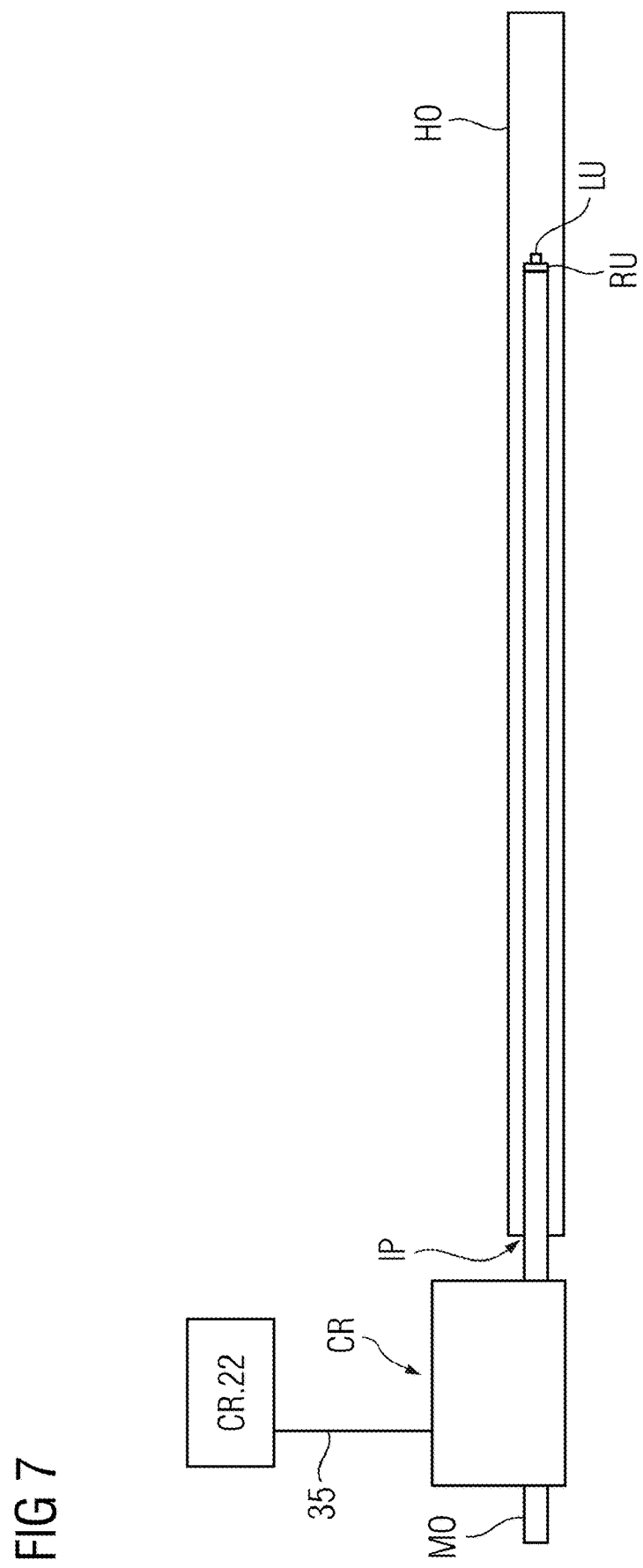
FIGS. 7 and 8 depict schematic diagrams of different forms of embodiment of a proposed system.

FIG. 7 shows a schematic diagram of an advantageous form of embodiment of a proposed system. In this case, the system may have a further processing unit CR.22, a movement apparatus CR, and a medical apparatus MO. The medical apparatus MO may further have a light emission unit LU and a receive unit RU. Moreover, the apparatus MO may be configured to be arranged at least partly above an insertion point IP, (e.g., an introduction tube), in an examination region, (e.g., a hollow organ HO), of an examination object. The light emission unit LU may further be configured, for emission of excitation light, in this case the excitation light, to excite an optoacoustic emission of ultrasound and/or an emission of fluorescent light. The receive unit RU and the light emission unit LU may further be arranged on a distal section of the apparatus MO. In this case, the receive unit RU may be configured to receive the ultrasound and/or the fluorescent light. The receive unit RU may further be configured for provision of a signal to the further processing unit CR.22 as a function of the received ultrasound. Furthermore, the further processing unit CR.22 may be configured to provide a control signal 35 for controlling the movement of the apparatus MO by the movement apparatus CR based on the signal.

The receive unit RU may advantageously have an ultrasound transducer TD and/or an optical sensor OS. In this case, the ultrasound transducer TD may be configured to receive the ultrasound. The optical sensor OS may further be configured to receive the fluorescent light.

Furthermore, the ultrasound transducer TD may be configured to emit further ultrasound and to receive the further ultrasound after an interaction with the examination region.

As an alternative, or in addition, the medical apparatus MO may be a proposed medical apparatus MO.

Moreover, the excitation light may be configured to excite a first and/or a second fluorescence dye in each case for optoacoustic emission of ultrasound and/or for emission of fluorescent light.

Figure 8:
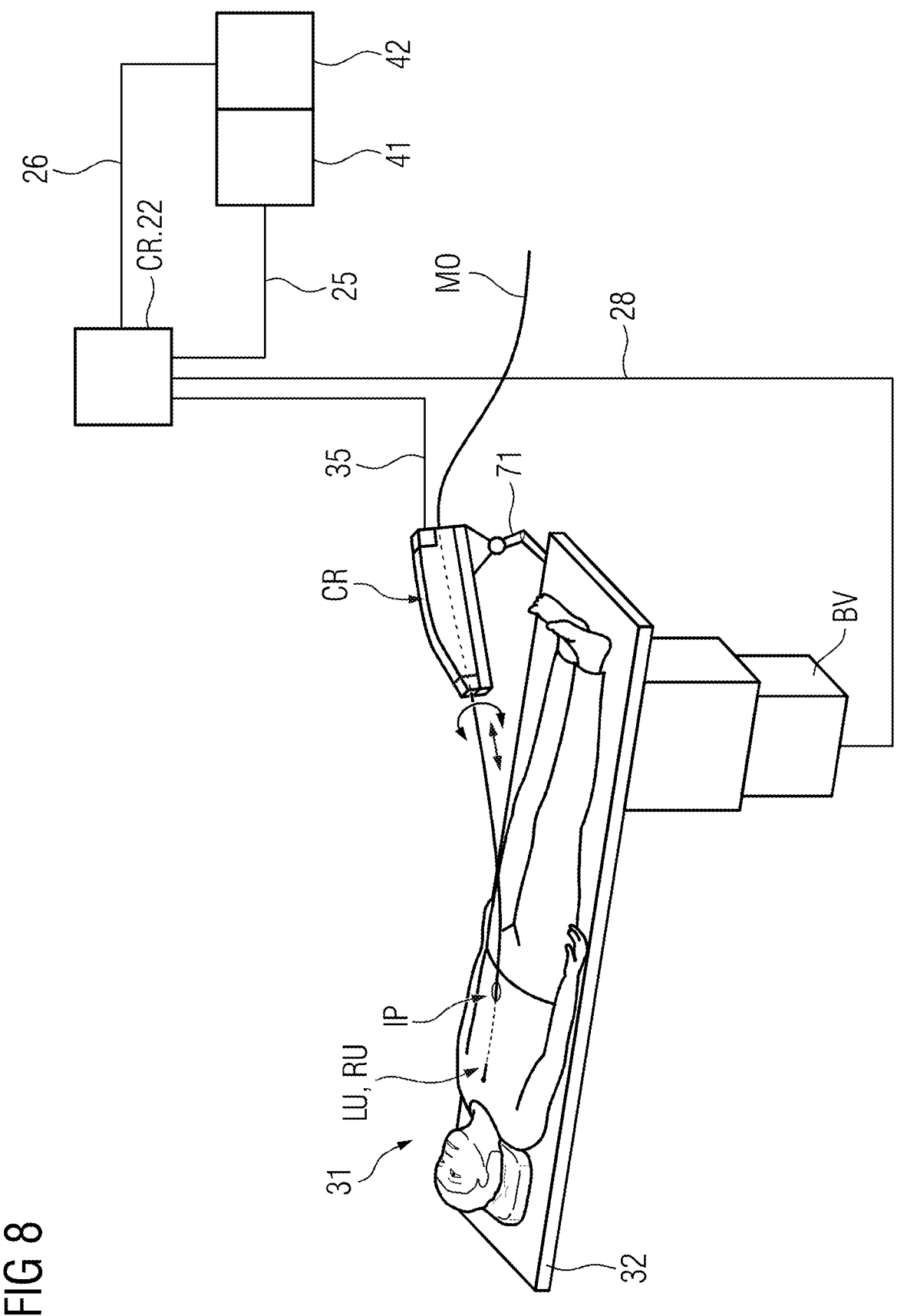

FIG. 8 shows a further advantageous form of embodiment of a proposed system. In this case the movement apparatus CR is configured for robotic movement of the medical apparatus MO. The movement apparatus CR may be configured, e.g., as a catheter robot, in particular for remote manipulation of the medical apparatus MO. Advantageously, the medical apparatus MO may be introduced via an introduction tube at the insertion point IP into the examination object 31 arranged on the patient support apparatus 32, in particular into the hollow organ HO of the examination object 31. In this case, the patient support apparatus 32 may be at least partly movable. For this the patient support apparatus 32 may advantageously have a movement unit BV, with the movement unit BV being controllable by a signal 28 from the further processing unit CR.22.

The movement apparatus CR may further be attached by an attachment element 71, e.g., a stand and/or robot arm, to the patient support apparatus 32, in particular movably. Advantageously, the movement apparatus CR may be configured to translationally move the medical apparatus MO arranged therein at least in a longitudinal direction of the medical apparatus MO. The movement apparatus CR may further be configured to rotate the medical apparatus MO around its longitudinal direction. As an alternative or in addition the movement apparatus CR may be configured for controlling a movement of at least one part of the medical apparatus MO, e.g., of the distal section and/or of the light emission unit LU and/or of the receive unit RU.

The system may further have an input unit 42 and a display unit 41. In this case, the input unit 42 may be configured for detecting an input of a user, in particular for controlling the movement apparatus CR and/or the medical apparatus MO. The input unit 42 may include a keyboard and/or a pointing device, in particular, a computer mouse. The input unit 42 may be configured to provide a signal 26 to the further processing unit CR.22 as a function of the detected input of the user. The display unit 41 may further include a monitor and/or a display. In this case, the input unit 42 may be integrated at least partly into the display unit 41, e.g., with a capacitive and/or resistive input display. The display unit 41 may be configured in particular to display a graphical representation of the pre-operative image dataset and/or of the dataset, which are registered with one another.

The control signal 35 for controlling the movement of the apparatus MO may further include at least one command for an, in particular step-by-step, control of the movement apparatus CR. In particular, the control signal 35 may include at least one command, (e.g., a chronological sequence of commands), for predetermining a, (e.g., simultaneous), translation and/or rotation of the medical apparatus MO, (e.g., of the distal section and/or of the light emission unit LU and/or of the receive unit RU), by the movement apparatus CR. The movement apparatus CR may advantageously be configured to position the medical apparatus MO based on the control signal 35, in particular to move it translationally and/or rotationally.

Figure 9:
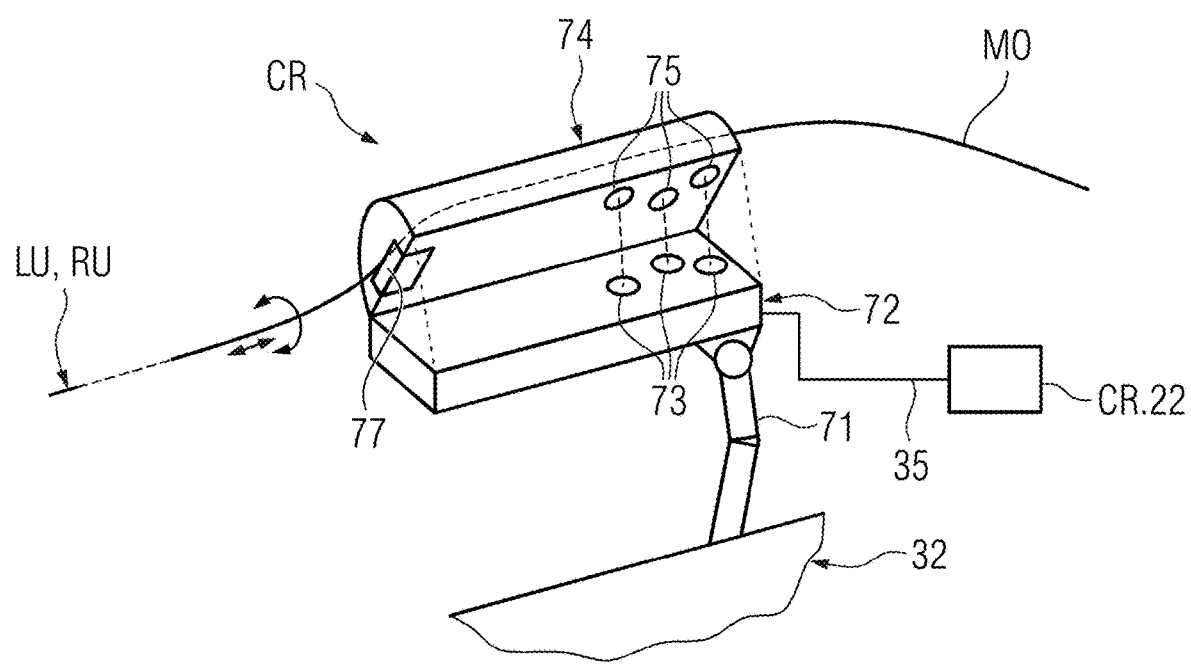
FIG. 9 depicts a schematic diagram of a movement apparatus.

FIG. 9 shows a schematic diagram of the movement apparatus CR for robotic movement of the medical apparatus MO. Advantageously, the movement apparatus CR may have a movable and/or drivable attachment element 71. The movement apparatus CR may further have a cassette element 74 configured to accommodate at least a part of the medical apparatus MO. The movement apparatus CR may further have a movement element 72, which is attached to the attachment element 71, e.g., a stand and/or robot arm. Moreover, the attachment element 71 may be configured to attach the movement element 72 to the patient support apparatus 32, in particular movably. The movement element 72 may further advantageously have at least one actuator element 73, in particular three actuator elements 73, e.g., an electric motor, wherein the further processing unit CR.22 is configured for control of the at least one actuator element 73. Advantageously, the cassette element 74 may be coupled in particular mechanically and/or electromagnetically and/or pneumatically to the movement element 72, in particular to the at least one actuator element 73. In this case, the cassette element 74 may further have at least one transmission element 75, which is movable through the coupling between the cassette element 74 and the movement element 72, in particular the at least one actuator element 73. In particular, the at least one transmission element 75 may be movement-coupled to the at least one actuator element 73. The transmission element 75 may further be configured to transmit a movement of the actuator element 73 to the medical apparatus MO in such a way that the medical apparatus MO is moved in its longitudinal direction and/or the medical apparatus MO is rotated around its longitudinal direction. The at least one transmission element 75 may have a pulley and/or roller and/or metal plate and/or shear plate.

Advantageously, the movement element 72 may have a number of, in particular independently controllable, actuator elements 73. The cassette element 74 may further have a number of transmission elements 75, in particular, at least one movement-coupled transmission element 75 for each of the actuator elements 73. This enables an, in particular independent and/or simultaneous, movement of the medical apparatus MO in various degrees of freedom of movement to be made possible.

The movement apparatus CR, in particular the at least one actuator element 73, may be controllable by the further processing unit CR.22 by the control signal 35. This enables the movement of the medical apparatus MO to be controlled, in particular indirectly, by the further processing unit CR.22. Moreover, an alignment and/or position of the movement apparatus CR relative to the examination object 31 may be adaptable by a movement of the attachment element 71. The movement apparatus CR is advantageously configured to receive the control signal 35.

Furthermore, the movement apparatus CR may advantageously have a sensor unit 77 configured to detect a relative movement of the medical apparatus MO relative to the movement apparatus CR. In this case, the sensor unit 77 may have an encoder, (e.g., a wheel encoder and/or a roller encoder), and/or an optical sensor, (e.g., a barcode scanner and/or a laser scanner and/or a camera), and/or an electromagnetic sensor. For example, the sensor unit 77 may be arranged integrated at least partly into the movement element 72, (e.g., the at least one actuator element 73), and/or the cassette element 74, (e.g., the at least one transmission element 75). The sensor unit 77 may be configured to detect the relative movement of the medical apparatus MO by detecting the medical apparatus MO relative to the movement apparatus CR. As an alternative, or in addition, the sensor unit 77 may be configured to detect a movement and/or change of location of components of the movement apparatus CR, with the components being movement-coupled to the medical apparatus MO, e.g., to the at least one actuator element 73 and/or to the at least one transmission element 74.

The schematic diagrams contained in the described figures in no way depict a scale or relative sizes.

In conclusion, the method described in detail above and also the apparatuses shown merely represent exemplary embodiments, which may be modified by the person skilled in the art in a wide diversity of ways without departing from the area of the disclosure. Furthermore, the use of the indefinite article "a" or "an" does not exclude the features concerned also being able to be present multiple times. Likewise, the terms "unit" and "element" do not exclude the components involved including a number of sub-components working together, which, if necessary, may also be spatially distributed.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A medical apparatus comprising:
    a light emission unit configured to emit excitation light, wherein the light emission unit comprises a light source and an optical fiber, wherein the optical fiber optically contacts the light source, and wherein the optical fiber has an end area for emission of the excitation light from the light source;
    an ultrasound transducer;
    an instrument channel; and
    a hollow needle,
    wherein the medical apparatus is configured to be arranged at least partly in an examination region of an examination object,
    wherein the excitation light is configured to excite an optoacoustic emission of an ultrasound,
    wherein the light emission unit is arranged at least partly in the hollow needle,
    wherein the hollow needle is arranged at least partly for movement in the instrument channel,
    wherein the instrument channel has an opening for bringing the hollow needle and the light emission unit out on a distal section of the medical apparatus,
    wherein the ultrasound transducer is arranged on the distal section of the medical apparatus,
    wherein the hollow needle is configured to puncture tissue in the examination region and to be moved out from the instrument channel at least partly through the opening of the instrument channel,
    wherein the hollow needle is configured to bring out the end area of the optical fiber of the light emission unit into the punctured tissue via an opening of the hollow needle such that the end area of the optical fiber is positioned outside of the hollow needle, and
    wherein the ultrasound transducer is configured for receiving the ultrasound.

2. The medical apparatus of claim 1, wherein the ultrasound transducer is further configured to emit a further ultrasound and to receive the further ultrasound after an interaction with the examination region.

3. The medical apparatus of claim 1, wherein the medical apparatus is further configured to reconstruct a spatially resolved dataset from the received ultrasound.

4. The medical apparatus of claim 3, further comprising:
    a display unit,
    wherein the medical apparatus is further configured to receive a pre-operative image dataset of the examination object, the pre-operative image dataset comprising an image of the examination region,
    wherein the medical apparatus is further configured to register the spatially resolved dataset with the pre-operative image dataset, and
    wherein the display unit is configured to show a graphical representation of the pre-operative image dataset and the spatially resolved dataset that are registered with one another.

5. The medical apparatus of claim 3, wherein the hollow needle, the light emission unit, the ultrasound transducer, or a combination thereof are movable and/or deformable, and
    wherein the medical apparatus is configured to control a movement and/or deformation of the hollow needle, the light emission unit, the ultrasound transducer, or a combination thereof as a function of the spatially resolved dataset.

6. The medical apparatus of claim 1, wherein the ultrasound transducer has a one-dimensional array or a two-dimensional array of transducer elements.

7. The medical apparatus of claim 1, wherein the ultrasound transducer has an annular opening for accommodating the hollow needle, and
    wherein the hollow needle is arranged at least partly in the annular opening.

8. The medical apparatus of claim 1, wherein the ultrasound transducer is coupled mechanically-movably to the instrument channel or is arranged in a fixed location with regard to the instrument channel.

9. The medical apparatus of claim 1, wherein the excitation light is configured to excite a first fluorescence dye for the optoacoustic emission of the ultrasound.

10. The medical apparatus of claim 1, further comprising:
    an optical sensor,
    wherein the excitation light is further configured to excite an emission of fluorescent light,
    wherein the optical sensor is configured to receive the fluorescent light.

11. The medical apparatus of claim 10,
    wherein the optical fiber further optically contacts the optical sensor, and
    wherein the end area of the optical fiber is further configured to receive the fluorescent light.

12. The medical apparatus of claim 10, wherein the excitation light is configured to excite a first and/or a second fluorescence dye in each case for the optoacoustic emission of the ultrasound and/or for the emission of the fluorescent light.

13. The medical apparatus of claim 1, wherein the light emission unit and/or the ultrasound transducer are movable in relation to the instrument channel,
    wherein the medical apparatus is configured to carry out a predefined movement of the light emission unit and/or of the ultrasound transducer, and
    wherein the medical apparatus is configured to reconstruct a spatial distribution of the received ultrasound based on a tomography algorithm.

* * * * *